United States Patent
Comte et al.

(10) Patent No.: US 11,530,185 B2
(45) Date of Patent: Dec. 20, 2022

(54) METHOD FOR PREPARING NITROPYRAZOLES

(71) Applicants: ARIANEGROUP SAS, Paris (FR); EURENCO, Sorgues (FR)

(72) Inventors: Sébastien Comte, Savigny le Temple (FR); Elsa Delmas, Toulouse (FR)

(73) Assignees: ARIANEGROUP SAS, Paris (FR); EURENCO, Sorgues (FR)

( * ) Notice: Subject to any disclaimer, the term of this patent is extended or adjusted under 35 U.S.C. 154(b) by 0 days.

(21) Appl. No.: 17/271,492

(22) PCT Filed: Aug. 30, 2019

(86) PCT No.: PCT/FR2019/052007
§ 371 (c)(1),
(2) Date: Feb. 25, 2021

(87) PCT Pub. No.: WO2020/043998
PCT Pub. Date: Mar. 5, 2020

(65) Prior Publication Data
US 2021/0198210 A1    Jul. 1, 2021

(30) Foreign Application Priority Data
Aug. 31, 2018 (FR) .................. FR1800916

(51) Int. Cl.
*C07D 231/16* (2006.01)

(52) U.S. Cl.
CPC ................ *C07D 231/16* (2013.01)

(58) Field of Classification Search
CPC .................................. C07D 231/16
See application file for complete search history.

(56) References Cited

FOREIGN PATENT DOCUMENTS

| | | |
|---|---|---|
| CN | 105669557 A | 6/2016 |
| EP | 2 130 821 A1 | 12/2009 |
| FR | 2 917 409 A1 | 12/2008 |

OTHER PUBLICATIONS

International Search Report as issued in International Patent Application No. PCT/FR2019/052007, dated Jan. 3, 2020.
Rao, E. N., et al., "Experimental and theoretical studies on the structure and vibrational properties of nitropyrazoles," Journal of Molecular Structure, vol. 1043, Apr. 2013, XP028564730, pp. 121-131.
EK, S., et al., "Four Syntheses of 4-Amino-3,5-dinitropyrazole," Journal of Heterocyclic Chemistry, vol. 51, No. 6, Nov. 2014, XP055576617, pp. 1621-1627.
Ravi, P., "Experimental and DFT studies on the structure, infrared and Raman spectral properties of dinitropyrazoles," Journal of Molecular Structure, vol. 1079, Sep. 2014, XP029083911, pp. 433-447.
Janssen, J. W. A. M., et al., "Pyrazoles. XII. The Preparation of 3(5)-Nitropyrazoles by Thermal Rearrangement of (N-Nitropyrazoles[1,2]," Journal of Organic Chemistry, May 1973, vol. 38, No. 10, pp. 1777-1782.

*Primary Examiner* — Shawquia Jackson
(74) *Attorney, Agent, or Firm* — Pillsbury Winthrop Shaw Pittman LLP

(57) ABSTRACT

A process for the sigmatropic rearrangement of the compound of formula

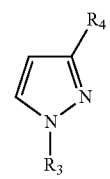

in which $R_3$ is an $NO_2$ group and $R_4$ is either a hydrogen or an $NO_2$ group, includes heat treating the compound by microwave.

7 Claims, 1 Drawing Sheet

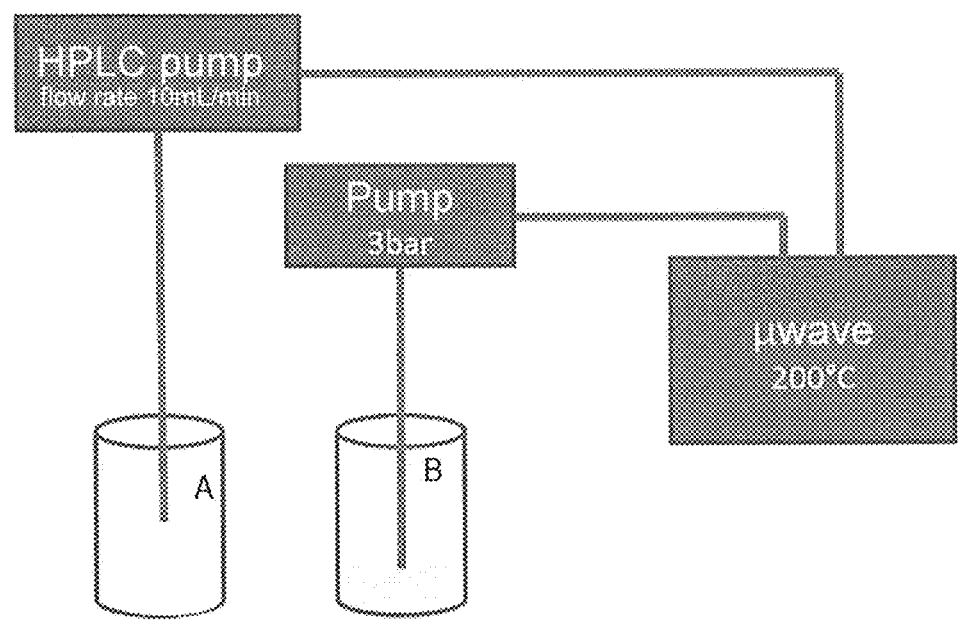

METHOD FOR PREPARING NITROPYRAZOLES

CROSS-REFERENCE TO RELATED APPLICATIONS

This application is the U.S. National Stage of PCT/FR2019/052007, filed Aug. 30, 2019, which in turn claims priority to French patent application number 1800916 filed Aug. 31, 2018. The content of these applications are incorporated herein by reference in their entireties.

Technical Field of the Invention

The invention relates to the field of energetic molecules which can be used in the manufacture of pyrotechnic charges. More particularly the invention relates to a process for preparing precursors of 3,4,5-trinitropyrazole.

Prior Art

Energetic molecules such as 3,4,5-trinitropyrazole (hereinafter "3,4,5-TNP") or derivatives of this compound (such as those described in EP-A-2 130 821) are suitable for the manufacture of pyrotechnic charges, owing to their advantageous properties in terms of performance and sensitivity, while retaining a high level of thermal stability, which is compatible with their use in the fields of propulsion and explosives.

One pathway to synthesis of 3,4,5-TNP, starting from 3,5-dinitropyrazole, is described in patent application FR-A-2 917 409. The 3,5-dinitropyrazole is obtained by sigmatropic rearrangement of 1,3-dinitropyrazole, which is itself obtained from 3-nitropyrazole, the latter being obtained by sigmatropic rearrangement of N-nitropyrazole. Operating conditions for the sigmatropic rearrangement of N-nitropyrazole are described, for example, in J. Org. Chem. 1973, 38(10), 1777-1782. These operating conditions (6 h at 160° C.) are considered to be restrictive for contemplating industrial scale-up. The result is a mediocre efficacy and a mediocre yield in the reaction for obtaining 3,4,5-TNP from N-nitropyrazole.

This finding has led the inventors to look for solutions for improving the operating conditions in the synthesis of 3,4,5-TNP.

BRIEF DESCRIPTION OF THE DRAWING

FIG. 1 represents an assembly used in the process of the invention.

DESCRIPTION OF THE INVENTION

Contrary to all expectations, the inventors have demonstrated the fact that it is possible to obtain a high yield for the steps of sigmatropic rearrangement of N-nitropyrazole and 1,3-dinitropyrazole when the starting compounds are heated using microwaves. To the knowledge of the inventors, no such means of heat treatment has ever been implemented in the synthesis of energetic molecules.

Thus, according to a first aspect, the invention relates to a process for preparing a compound of formula (VIIa):

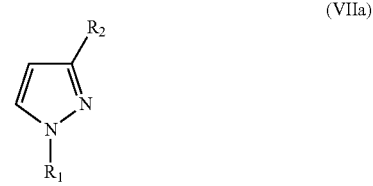

in which the pair ($R_1$, $R_2$) is either (H, $NO_2$) or ($NO_2$, $NO_2$), which comprises the microwave thermal treatment of a compound of formula (VIIb):

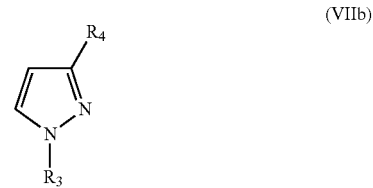

in which $R_3$ is an $NO_2$ group and $R_4$ is either a hydrogen or an $NO_2$ group.

The step of sigmatropic rearrangement of the compound of formula (VIIb) is advantageously performed in a solvent which can be used for carrying out a subsequent step of in situ nitration of the compound of formula (VIIa), in other words a solvent which is an $NO_2^+$ cation promoter.

In one embodiment of the invention, the compound of formula (VIIb) is dissolved in a benzenic solvent, such as xylene, bromobenzene or dichlorobenzene, or in an "acetic" solvent such as acetic acid or acetic anhydride, the latter two being preferred on account of their capacity to be $NO_2+$ cation promoters. The concentration of the compound of formula (VIIb) is advantageously from about 50 to about 500 g/L.

In one embodiment of the invention, the duration of the heat treatment is from about 1 min to about 1 h, preferably from about 1 min to about 45 min, preferably from about 1 min to about 30 min, preferably from about 1 min to about 15 min, preferably from about 1 min to about 10 min.

In one embodiment of the invention, the heat treatment of the compound of formula (VIIb) is such that the temperature of the reaction mixture is from about 150° C. to about 220° C., preferably from about 150° C. to about 200° C., more preferably from about 180° C. to about 200° C. After cooling, the expected product of formula (VIIa) precipitates in the cold and is then recovered by techniques well known to the skilled person; if no precipitation is observed in the cold, adding water allows the product to be precipitated. In either case the yield of compound of formula (VIIa) is from about 60% to about 100%.

The compounds of formula (VIIa) are intermediates in the synthesis of 3,5-dinitropyrazole.

Therefore, according to another aspect, the invention relates to a process for preparing the compound of formula (II):

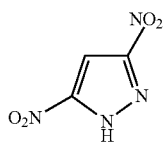

which comprises the steps of:
a) nitration of the compound of formula (VI):

to give the compound of formula (V):

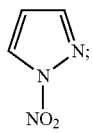

b) microwave heat treatment of the compound of formula (V), to give the compound of formula (IV):

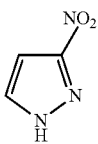

c) nitration of the compound of formula (IV) to give the compound of formula (III):

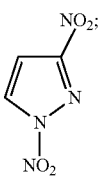

d) microwave heat treatment of the compound of formula (III), to give the compound of formula (II).

The step of nitration of each of the compounds of formula (VI) and of formula (IV) is performed in a manner known to the skilled person, typically by contacting the compound in question with nitric acid and optionally with water, in a suitable solvent. As indicated above for the first aspect of the invention, the solvent used may be a benzenic solvent, such as xylene, bromobenzene or dichlorobenzene, or an "acetic" solvent such as acetic acid or acetic anhydride, with acetic acid being preferred.

As indicated above for the first aspect of the invention, the duration of the heat treatment of each of the compounds of formula (V) and of formula (III) is from about 1 min to about 1 h, preferably from about 1 min to about 45 min, preferably from about 1 min to about 30 min, preferably from about 1 min to about 15 min, preferably from about 1 min to about 10 min.

As indicated above for the first aspect of the invention, the heat treatment of the compounds of formula (V) and (III) is such that the temperature of the reaction mixture is from about 150° C. to about 220° C., preferably from about 150° C. to about 200° C., more preferably from about 180° C. to about 200° C.

In one embodiment of this first aspect of the invention, each of steps a) to d) is performed in the presence of the same solvent, advantageously selected from a benzenic solvent, such as xylene, dichlorobenzene or bromobenzene; acetic acid; or acetic anhydride. The solvent used in each of steps a) to d) is preferably a solvent which enables a subsequent step of in situ nitration of the compound of formula (IV) and/or of the compound of formula (II), with acetic acid or acetic anhydride being particularly suitable for this purpose. An embodiment of this kind opens up the possibility of continuous synthesis of the compound of formula (II), with the reduction in the amount of solvent to be reprocessed/removed.

The compound of formula (II) is itself an intermediate in the synthesis of the 3,4,5-trinitropyrazole of formula (I):

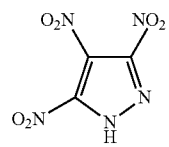

Therefore, according to another aspect, the invention relates to a process for preparing 3,4,5-trinitropyrazole, which comprises nitration of the compound of formula (II). This nitration is carried out according to techniques known to the skilled person, for example by reaction of the compound of formula (II) with nitric acid in the presence of sulfuric acid.

A better understanding of the invention will be obtained from the examples below, which are given purely by way of illustration. The thermal analysis of the compounds synthesized took place by differential scanning calorimetry (DSC) using a Mettler Toledo DSC3 instrument. The NMR spectra were obtained using a Bruker 400 MHz spectrometer with Avance III HD console.

Example 1

210 mg of N-nitropyrazole were introduced into a reaction tube with 4 mL of bromobenzene. After the tube had been sealed, it was heated in a microwave reactor to 200° C. (power: 150 W) for 5 minutes, the pressure inside the tube being stable at around 2 bar. After cooling, the precipitated product was filtered and dried under vacuum. This gave 210 mg of product, which, after NMR analysis, corresponds to 3-nitropyrazole (100% yield).

DSC (8° C./min): m.p.: 175.6° C.; evaporation: 250° C.
$^1$H NMR (DMSO): 7.04 (d, 1H), 8.04 (d, 1H), 13.96 (s (broad), NH)
$^{13}$C NMR (DMSO): 101.9 (CH(4)), 132.3 (CH), 156.3 (C—NO$_2$).

Example 2

210 mg of N-nitropyrazole were introduced into a reaction tube with 4 mL of acetic acid. After the tube had been sealed, it was heated in a microwave reactor to 200° C. (power: 150 W) for 5 minutes, the pressure inside the tube being stable at around 3 bar. After cooling, the precipitated product was filtered and dried under vacuum. This gave 200 mg of product, which, after NMR analysis, corresponds to 3-nitropyrazole (95% yield).

DSC (8° C./min): m.p.: 175.6° C.; evaporation: 250° C.
$^1$H NMR (DMSO): 7.04 (d, 1H), 8.04 (d, 1H), 13.96 (s (broad), NH)
$^{13}$C NMR (DMSO): 101.9 (CH(4)), 132.3 (CH), 156.3 (C—NO$_2$).

Example 3

210 mg of 1,3-dinitropyrazole were introduced into a reaction tube with 4 mL of acetic anhydride. After the tube had been sealed, it was heated in a microwave reactor to 200° C. (power: 150 W) for 5 minutes, the pressure inside the tube being stable at around 3 bar. After cooling, a solid product precipitated which, after NMR analysis, corresponds to 3,5-dinitropyrazole (60% yield).

DSC (8° C./min): m.p.: 169.9° C.; evaporation: 245° C.
$^1$H NMR (acetone): 7.81 (s, 1H)
$^{13}$C NMR (acetone): 100.2 (CH(4)), 152.3 (C—NO$_2$).

For comparison, the yield of the sigmatropic rearrangement reaction of 1,3-dinitropyrazole, performed by conventional heating, is about 40%.

Examples 4 to 6 took place using an assembly, shown in FIG. 1, composed of a vessel containing the reaction mixture A (typically, N-nitropyrazole or 1,3-dinitropyrazole), an HPLC pump, an 80 mL microwave reactor (millireactor type), a pressure regulation valve for maintaining the assembly at 3 bar, and a receiver flask B. The microwave reactor is a thick glass tube with a top-mounted introduction head and with a magnetic bar. The introduction head receives the inlet and outlet connections of the reactor. The inlet connection is a dip connection, meaning that the reactant is introduced at the bottom of the tube, and then, by the thrust effect of the pump, the product emerges at the top of the tube via the outlet connection in the direction of the backpressure regulator, which is set to a pressure of 3 bar. The receiving flask itself is a flask or a bottle made of glass, or else a condenser with a downstream suction filter for continuous separation of solvent from the end product.

Example 4

The assembly was placed in operation with pure bromobenzene so as to reach a temperature of up to 200° C. with a power of 300 W and a flow rate of 10 mL/min. When the assembly was at temperature and pressure, the reactor was fed with a 50 g/L solution of N-nitropyrazole. The precipitated product was recovered, after the assembly had been brought to atmospheric pressure and the temperature reduced. NMR analysis confirmed that the product obtained corresponds to 3-nitropyrazole (80% yield). The assembly operated for an hour without interruption, with a production of 30 g.

DSC (8° C./min): m.p.: 175.6° C.; evaporation: 250° C.
$^1$H NMR (DMSO): 7.04 (d, 1H), 8.04 (d, 1H), 13.96 (s (broad),NH)
$^{13}$C NMR (DMSO): 101.9 (CH(4)), 132.3 (CH), 156.3 (C—NO$_2$).

Example 5

The assembly was placed in operation with pure acetic anhydride so as to heat to temperature with a power of 300 W and a flow rate of 10 mL/min. When the assembly was at temperature and pressure, the reactor was fed with a 50 g/L solution of N-nitropyrazole. The product which precipitated after addition of water was recovered, after the assembly had been brought to atmospheric pressure and the temperature reduced. NMR analysis confirmed that the product obtained corresponds to 3-nitropyrazole (60% yield). The assembly operated for an hour without interruption, with a production of 30 g.

DSC (8° C./min): m.p.: 175.6° C.; evaporation: 250° C.
$^1$H NMR (DMSO): 7.04 (d, 1H), 8.04 (d, 1H), 13.96 (s (broad),NH)
$^{13}$C NMR (DMSO): 101.9 (CH(4)), 132.3 (CH), 156.3 (C—NO$_2$).

Example 6

In a first stage, a mixture of acetic anhydride (1 L) and nitric acid (47 g, i.e. 1 eq.) was prepared, with the temperature of the reaction mixture being kept below 10° C. Pyrazole (50 g) was then added in a number of portions, with the temperature of the reaction mixture being kept below 10° C. The reaction mixture was subsequently left with stirring for 30 minutes at a temperature of between 5 and 10° C. The mixture was then diluted in water (250 mL) so as to neutralize the reactive (nitrating) species, without the product of the reaction (N-nitropyrazole) precipitating from the solution.

In parallel, the assembly described above was heated to temperature with acetic anhydride, with regulation of the power of 300 W and a flow rate of 10 mL/min. When the assembly was at temperature and pressure, the reactor was fed with an approximately 50 g/L solution of N-nitropyrazole. The product which precipitated was recovered, after the assembly had been brought to atmospheric pressure and the temperature reduced. NMR analysis confirmed that the product obtained corresponds to 3-nitropyrazole (60% yield). The assembly operated for an hour without interruption, with a production of 30 g.

DSC (8° C./min): m.p.: 175.6° C.; evaporation: 250° C.
$^1$H NMR (DMSO): 7.04 (d, 1H), 8.04 (d, 1H), 13.96 (s (broad),NH)
$^{13}$C NMR (DMSO): 101.9 (CH(4)), 132.3 (CH), 156.3 (C—NO$_2$).

The invention claimed is:
1. A process for preparing a compound of formula (II):

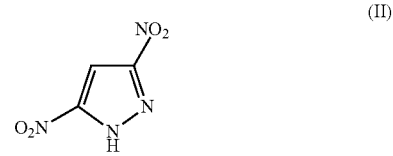 [SMILES: O=[N+]([O-])c1cc([N+](=O)[O-])[nH]n1]

which comprises the steps of:
a) subjecting a compound of formula (VI) to nitration:

to give a compound of formula (V):

b) heat-treating by microwave the compound of formula (V), to give a compound of formula (IV):

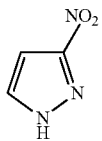

(IV)

c) subjecting the compound of formula (IV) to nitration, to give a compound of formula (III):

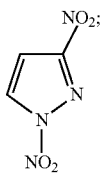

(III)

d) heat-treating by microwave the compound of formula (III), to give the compound of formula (II).

2. The process of claim 1, wherein each of steps a) to d) is performed in the presence of a solvent selected from the group consisting of a benzenic solvent; acetic acid; and acetic anhydride.

3. The process of claim 2, wherein the benzenic solvent is xylene, dichlorobenzene or bromobenzene.

4. The process of claim 2, wherein each of steps a) to d) is performed in the presence of the same solvent, which is either acetic acid or acetic anhydride.

5. The process of claim 1, wherein the duration of the heat treatment is from about 1 min to about 1 h in each of steps b) and d).

6. The process of claim 1, wherein the temperature during the heat treatment of the compounds of formula (V) and (III) is in the range from about 150° C. to about 220° C.

7. The process of claim 1, wherein steps a) and c) are performed in the presence of nitric acid and optionally water.

* * * * *